(12) United States Patent
Portello et al.

(10) Patent No.: US 6,187,758 B1
(45) Date of Patent: Feb. 13, 2001

(54) ANTHRACYCLINE GLYCOSIDES

(75) Inventors: Cinzia Portello, Caronno Pertusella-Varese; Emanuele Arlandini, Milan; Umberto Breme, Vigevano Pavia; Anna Luisa Colombo, Milan; Giuliano Franchi, Milan; Giuliano Oronzo, Milan; Marco Tató, Milan; Luisa Garofano, Milan; Marina Ciomei, Pavia, all of (IT)

(73) Assignee: Pharmacia & Upjohn S.p.A., Milan (IT)

( * ) Notice: Under 35 U.S.C. 154(b), the term of this patent shall be extended for 0 days.

(21) Appl. No.: 09/367,848

(22) PCT Filed: Nov. 27, 1998

(86) PCT No.: PCT/EP98/07773

§ 371 Date: Aug. 27, 1999

§ 102(e) Date: Aug. 27, 1999

(87) PCT Pub. No.: WO99/35153

PCT Pub. Date: Jul. 15, 1999

(30) Foreign Application Priority Data

Dec. 31, 1997 (GB) .................................................. 9727546

(51) Int. Cl.$^7$ .......................... A61K 31/71; C07H 15/24; C12P 19/56
(52) U.S. Cl. ................................ 514/34; 536/6.4; 435/78
(58) Field of Search ............................... 435/78; 536/6.4; 574/34

(56) References Cited

U.S. PATENT DOCUMENTS 3,590,028 * 6/1971 Arcamone et al. .................... 536/6.4
4,077,844 * 3/1978 Marshall et al. ........................ 435/71

FOREIGN PATENT DOCUMENTS 844 318   11/1980   (BE) .
27 24 441   12/1977   (DE) .
0 239 774   10/1987   (EP) .

\* cited by examiner

*Primary Examiner*—Elli Peselev
(74) *Attorney, Agent, or Firm*—Oblon, Spivak, McClelland, Maier & Neustadt, P.C.

(57) ABSTRACT

An anthracycline glycoside of formula I

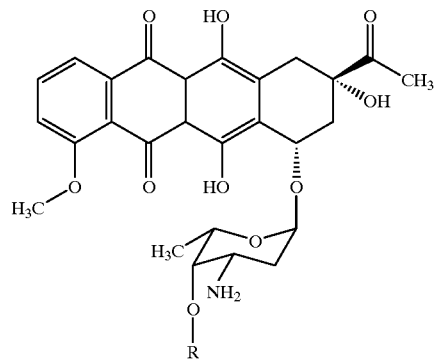

wherein R is one of the two following residues:

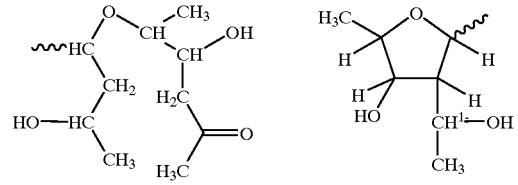

or a pharmaceutically acceptable salt thereof.

10 Claims, No Drawings

ANTHRACYCLINE GLYCOSIDES

The present invention relates to anthracycline glycosides, their isolation and pharmaceutical compositions containing them.

The present invention provides anthracycline glycosides of formula I:

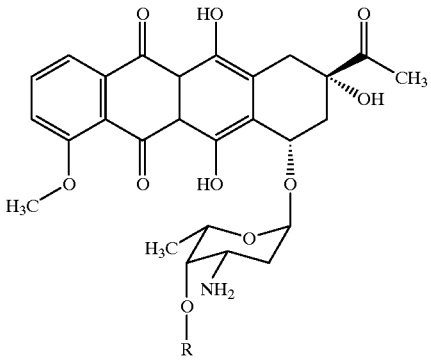

wherein R represents one of the two following residues:

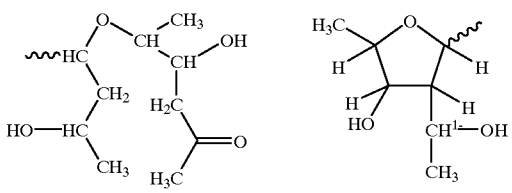

or a pharmaceutically acceptable salt thereof. The compounds of the invention are anti-tumour agents. The new anthracyclines are useful as remedies for gram positive and gram negative bacterial infections and they inhibit growth of tumor cells.

The preferred compounds according to the present invention are in particular:
compound A:
4'-O-[3"-hydroxy-1"-(2'"-hydroxy-1'"-methyl-4'"-oxo-pentyloxy)-butyl]-daunorubicin of formula:

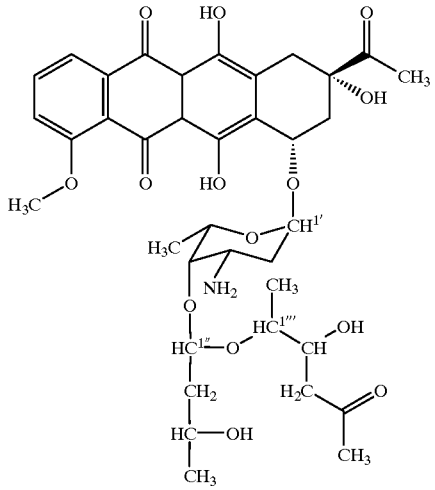

and compound B:
4'-O-[4"-hydroxy-3"-(1'"-hydroxy-ethyl)-5"-methyl-tetrahydrofuran-2-yl]-daunorubicin of formula:

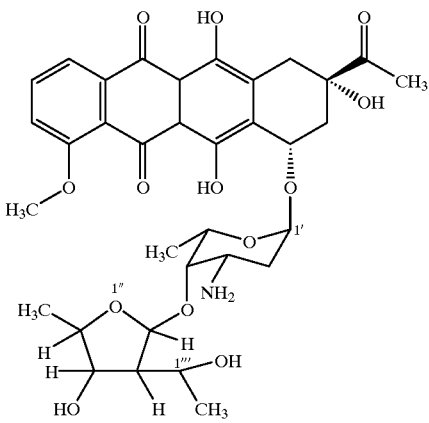

The present invention further provides a process for the preparation of an anthracycline glycoside of formula I or a pharmaceutically acceptable salt thereof, which comprises culturing *Streptomyces peucetius*, in particular *Strepromyces peucetius* ATCC 27952, and isolating a resultant anthracycline glycoside of formula I as such or in the form of a pharmaceutically acceptable salt thereof. The anthracycline glycosides of this invention may be obtained therefore by culturing *Streptomyces peucetius* in a culture medium containing a carbon source, nitrogen source, inorganic components and, optionally micro-components under aerobic conditions. They may be isolated by conventional procedures such as solvent extraction, column chromatography, salt formation, preparative thin layer chromatography (TLC) and/or crystallization.

Thus, the present invention also provides a process for preparing a compound of the formula I as above defined, or a pharmaceutically acceptable salt thereof by means of fermentation, extraction and purification.

The pharmaceutically acceptable salts of the compounds of formula (I) include salts with pharmaceutically acceptable acids, either inorganic acids, for example, hydrochloric, hydrobromic, nitric or sulphuric acid; or organic acids, for example, citric, tartaric, maleic, fumaric, methanesulfonic or ethanesulfonic acid.

Preferred salts according to the invention are hydrochlorides.

The new anthracycline derivatives of the present invention are endowed with useful antitumoral activity.

The present invention also provides a pharmaceutical composition comprising a pharmaceutically acceptable diluent or carrier and, as an active principle, an anthracycline analogue of formula I or a pharmaceutically acceptable salt thereof.

Fermentation process.

The production was carried out by well known methods. The micro-organism was cultured in a previously sterilized liquid culture medium under aerobic conditions at a temperature ranging from 25 to 35° C. (preferably at 30° C.) over a period of time varying from 5 to 8 days (preferably 7 days) and a pH value which initially was from 6.5 to 7.0 and at the end of the fermentation process from 5 to 7.0.

The culture medium consisted of a carbon and a nitrogen source as well as of mineral salts.

As carbon source starch, dextrin, glucose, maltose can be used.

As nitrogen source sorbean meal, dry yeast, meat, peptone or casein can be used.

All ammonium salts such as ammonium nitrate, ammonium sulphates, ammonium phosphates may be used.

The mineral salts useful for the production may vary depending on the medium employed.

The fermentation may be carried out in flasks or in pilot scale fermenters of various capacities.

Extraction Procedure.

At the end of the fermentation process the new anthracycline glycosides were principally found in the mycelium which was separated from the fermentation supernatant by filtration at pH 7.5.

The mycelium was extracted with water-miscible organic solvents such as acetone and methanol and then the mycelial extracts were concentrated in vacuo to obtain an aqueous solution. After adjusting to pH 7.2 the aqueous solution was loaded on Amberlite column. The selected fractions obtained were concentrated in vacuo and then extracted in alkaline conditions with dichloromethane. The organic extracts were concentrated to a small volume and then precipitated by addition of petroleum ether to obtain a crude extract.

Purification Procedure

The purification procedure consists of conventional methods like column chromatography, preparative TLC and crystallization.

The crude extract obtained from the Extraction Procedure was chromatographed on a silica gel column eluted by step elution with methanol. The fractions obtained were monitored by TLC and the selected fractions were concentrated in vacuo to give a red powder. This powder may be purified by flash chromatography on silica gel or by preparative TLC in order to obtain sufficiently pure anthracycline glycosides to determine their structure by mass spectrometry and NMR analysis and to study their biological activity. The resultant compound may be then converted into a pharmaceutically-acceptable salt.

Biological Activity

A) Antibacterical activity

The "in vitro" minimun inhibitory concentration (MIC) of the novel anthracycline glycosides in comparison with daunorubicin was determined for some microoganisms using the standard tube dilution procedure and is reported in Table 1.

TABLE 1

Antibacterial activity

| Microorganism | MIC in μg/ml | |
|---|---|---|
| | Daunorubicin | Compound A |
| *Staphylococcus aureus* ATCC 14154 | 25 | 6.25 |
| *Staphylococcus aureus* ATCC 65389 | 6.25 | 3.12 |
| *Bacillus subtilis* ATCC 6633 | 3.12 | 1.56 |
| *Bacillus cereus* ATCC 9634 | 6.25 | 1.56 |
| *Sarcina lutea* ATCC 9341 | 3.12 | 0.78 |
| *Micrococcus flavus* ATCC 10240 | 6.25 | 1.56 |
| *Candida albicans* ATCC 10231 | >100 | >100 |
| *Escherichia coli* K12 | >100 | >100 |
| *Klebsiella pneumoniae* ATCC 10031 | 50 | 25 |

B) Cytotoxic activity

The cytotoxic activity of the novel anthracycline glycosides was tested "in vitro" in comparison with daunorubicin on cultured L1210 cells as shown in Table 2.

TABLE 2

Cytotoxic activity of the novel anthracycline glycosides on the growth of L1210 cells

| Product | $IC_{50}$ (μg/ml) |
|---|---|
| Daunorubicin | 0.259 |
| Compound A | 0.085 |
| Compound B | 0.222 |

The cytotoxic activity of compound A and compound B has also been evaluated in comparison to Doxorubicin on a panel of solid human tumor cell lines: 4 human mammary adenocarcinoma cell lines (MCF-7, MCF-7/Dx, SKBR-3 and MDA-MB-231, 2 human ovarian carcinoma cell lines (A2780 and OVCAR3) and 2 human colon adenocarcinoma cell lines (HCT116 and, HT29). Cytotoxicity was evaluated by the SRB assay (J.N.C.I.: 82, 1107–1112 and 1113–1118, 1990) in 96 well plates at 72 h after treatment with different concentrations of the compounds. Concentrations inhibiting the growth by 50% (IC50 values) were calculated. The results are reported in Table 3. Both compunds are more potent than Doxorubicin on all the tested cell lines. In particular compound A is active also on the MCF7 clone resistant to Doxorubicin and is particularly potent ($IC_{50}$<10 nM) on 2 breast carcinoma cell lines (SKBR-3 and MDA-MB-23) and on both tested colon and ovarian carcinoma cell lines.

TABLE 3

Cytotoxic activity of the novel anthracycline glycosides on solid human tumor cell lines

| | DOXORUBICIN ($IC_{50}$ nM) | COMPOUND A ($IC_{50}$ nM) | COMPOUND B ($IC_{50}$ nM) |
|---|---|---|---|
| mammary carcinoma cell lines: | | | |
| MCF7 | 940 ± 400 | 15 | 100 |
| MCF7/DX | >10000 | 100 | >200 |
| SKBR-3 | 110 ± 20 | 1.4 | 8.9 |
| MDA-MB-231 | 540 ± 270 | 0.03 | 4.67 |
| colon adenocarcinoma cell lines: | | | |
| HCT 116 | 80 ± 20 | 0.3 | 4.8 |
| HT29 | 160 ± 50 | 3.2 | 11.2 |
| ovarian carcinoma cell lines: | | | |
| A2780 | 250 ± 140 | 0.4 | 7.5 |
| OVCAR-3 | 140 ± 10 | 0.08 | 20 |

Suitable routes of administration include parenteral administration, for example intravenous administration. For parenzeral administration a liquid formulation may be prepared using the anthracycline glycoside of formula I or salt thereof and a sterile diluent or carrier which may either dissolve the active compound or provide a suspension for it. The parenteral formulation may be prepared in the form of a sterile solid for reconstitution prior to administration with a suitable vehicle such as physiological saline, sterile water or other sterile vehicle.

The compounds of the invention are useful as anti-tumour agents and therefore can be used in methods of treatment of leukaemia or solid tumors.

A human or animal suffering from a tumour may be treated by a method which comprises the administration thereto of an effective amount of an anthracycline glycoside of formula I or pharmaceutically acceptable salt thereof. The condition of the human or animal may thereby be improved.

Examples of tumours that can be treated are sarcomas, carcinomas, lymphomas, neuroblastomas, melanomas, myelomas, Wilms tumour, leukaemias and adenocarcinomas. The compounds of the invention can be used to treat ovarian cancer, platinum-resistant cancer, metastatic breast cancer, non-small cell lung cancer and head and neck cancer.

A therapeutically effective amount of an anthracycline glycoside of formula I or salt thereof is administered to a human or animal patient having a tumor to ameliorate or improve the condition of the patient. An amount sufficient to inhibit the growth of the tumor may be administered. The dosage to be given can be ascertained using known dosage ranges for doxorubicin and daunorubicin modified by reference to the activity shown by the present compounds in in vitro and in vivo anti-tumor tests. Suitable dosages are generally in the range of 0.01 to 100 mg/m$^2$ body surface, preferably from 0.1 to 10 mg/m$^2$, depending on the nature and severity of the disease being treated and on the general condition of the patient.

The following Examples and Preparations are intended to illustrate the invention without limiting it.

Preparation a

A culture of *Streptomyces peucetius* strain ATCC 27952 has been grown for 12 days at 28° C. on agar slants of the following maintenance medium (CZY medium, % are by weight): sucrose 3%r, yeast extract 0.4%, NaNO$_3$ 0.3%, K$_2$HPO$_4$ 0.1%, MgSO$_4$.7H$_2$O 0.05%, KCl 0.05%, FeSO$_4$.7H$_2$O 0.001%, agar 2%, tap water up to 100 ml; pH 7.3 . Sterilization was performed by heating in an autoclave at 1200C for 20 minutes. The spores of the culture, generated on the surface of the solid medium, were collected and suspended in 1 ml of distilled water. The suspension so obtained was agitated to provide homogeneity and then inoculated in 300 ml Erlenmeyer flasks containing 30 ml of the following liquid growth medium: dextrine 2%, cornsteep liquor 1%, (NH$_4$)$_2$SO$_4$ 0.1%; K$_2$HPO$_4$ 0.01%, CaCO$_3$ 0.5%; tap water up to 100 ml. Sterilization was performed by heating in a autoclave at 120° C. for 20 minutes. The pH value of this medium after sterilization is between 6.5 and 7.0. The inoculated flasks are shaken for 2 days at a temperature of 280C on a rotary shaker running at 280 rpm and describing a circle of 7 cm in diameter.

1.5 ml of the culture grown as described above were inoculated in 300 ml flasks containing 30 ml of the following production medium (% are by weight): starch 6%, glucose 3%., dry yeast 1.5%, soya bean meal 1%, NaCl 0.2%, CaCO$_3$ 0.3%, MgSO$_4$ 0.01%, FeSO$_4$.7H$_2$O 0.01%, CuSO$_{4.7}$H$_2$O 0.01%, ZnSO$_4$.7H$_2$O 0.01%; tap water up to 100 ml. The medium was sterilized by heating in autoclave at 120° C. for 20 minutes. The pH value of this medium after sterilization is 6.4. The flasks were incubated at 30° C. for 7 days on a rotary shaker under the same conditions of the seed phase.

Preparation b

The whole broth (4 L) from a fermentation obtained according to Preparation a, was separated into supernatant fluid and mycelium by filtration after adjustment of pH to 7.5 with NaOH 1 M. Diatomaceus earth was used as filter aid. The mycelium was extracted two times with 3 liters of acetone and one time with 3 liters of Methanol (pH 5.3). The extracts were combined and concentrated in vacua. The resulting aqueous solution was adjusted to pH 7.2 with 1 M NaOH and after filtration was loaded on a Amberlite XAD2 column. After washing with water the column was eluted by step elution with Methanol.

The pigmented eluate was pooled and concentrated in vacua and then extracted in alkaline conditions with dichloromethane.

The organic layers were evaporated in vacuo to a small volume and then a crude extract was obtained by petroleum ether precipitation.

Preparation c 6.7 grams of the crude extract obtained according to preparation b starting from 140 L of fermentation broth, containing the new anthracycline glycosides, Compound A and Compound B, were dissolved in a small volume of dichloromethane and loaded on a silica gel dry column (silica gel 60; 70–230 Mesh ASTM; particle size 0.063–0.200 mm Merck). After washing with dichloromethane, the column was eluted by step elution with Methanol (10° % to 40%). The fractions obtained from the silica gel column were monitored by TLC. Some of them contained the compound A and others the compound B.

Analytical Methods

Samples of crude extract and samples obtained by purification steps were subjected to thin layer chromatography (TLC) using as eluent the following solvent systems:
1) Dichloromethane: Methanol 10:1 (by volume)
2) Dichloromethane: Methanol: Acetic acid 80:20:4 (by volume)
3) Dichloromethane: Methanol: Toluene 70:3:3 (by volume)

TLC plates are: Silica gel 60 F 205 (Merck Co)

The Rf values of the compound A and of the compound B developed with the three solvent systems are shown in the following table.

| SOLVENT SYSTEM | Rf VALUE Compound A | Rf VALUE Compound B |
| --- | --- | --- |
| 1 | 0.28 | 0.07 |
| 2 | 0.83 | 0.54 |
| 3 | 0.52 | 0.32 |

EXAMPLE 1

Fractions obtained according to preparation c containing the compound A, was dried in vacuo to get a brown-purple powder. This powder was dissolved in a small volume of dichloromethane and purified by flash chromatography on silica gel (silica gel 60 for flash chromatography; 230–400 Mesh ASTM; particle size 0.040–0.063 mm Merck ) The column was washed with dichloromethane and then the elution was carried out by step elution with Methanol (1 to 5° O). Selected fractions, picked by TLC, containing the Compound A, after concentration in vacuo to a small volume were precipitated with petroleum ether to obtain about 50 mg.

EXAMPLE 2

Fractions obtained according to preparation c, containing the compound B was dried in vacuo to give a brown-purple powder. This powder was dissolved in a small volume of dichloromethane and subjected to preparative TLC (silica gel 60F 250 20×20 cm×1 mm) using as eluent the solvent system 2 (as described in analytical methods).

The Compound B showed a medium Rf value of 0.54. This band was eluted with Methanol, washed with water and subsequently extracted with dichloromethane in alkaline conditions. After precipitation with petroleum ether 2 mg of compound B was obtained.

Chemical and Physical Properties

Purified samples were subjected to mass spectrometry, NMR and IR analyses using the following conditions:

FAB (fast atom bombardment) mass spectra were recorded on a Varian Mat 311-A mass spectrometer equipped with an Jon Tech FAB gun. The substance was dissolved in dithiothreitol/dithioerythritol=5/1 acidified with 2 N trifluoroacetic acid (TFA); the source temperature was 45° C., xenon was the bombarding gas and the kinetic energy of atoms was about 9 Kev.

FD (field desorption) mass spectra were recorded on a Varian Mat 311-A mass spectrometer equipped with a combined field ionization (FI)/FD/EI ion source using Benzonitrile activated emitters. The total potential difference between the field emitter anode and the cathode was 9 Kev. The emitter heating current was 31 mA and the source temperature was 100° C.

Spectra have been normalized starting from the value of 100 m/Z. IR spectra were recorded with a Parkin-Elmer model 1420 Spectrophotometer. NMR spectra were recorded on a Varian Unity-600 Spectrophotometer. Compound A and compound B obtained as fine red powder are soluble in acetone; slighty soluble in chloroform, dichloromethane, methanol; barely soluble or insoluble in ethyl ether, n-hexane, petroleum ether.

They are unstable in acidic media. On mild hydrolysis (40% v/v 0.1N HCl for 1–2 h at 60° C.) both the compound A and the compound B gave daunorubicin.

The physico-chemical properties of the compound A and compound B are shown in table 4, 5 and 6.

TABLE 4

Chemical and physical properties

| PROPERTIES | Compound A | Compound B |
|---|---|---|
| I.R. Spectrum (KBr) peacks at cm$^{-1}$ | 3480, 2970, 2930, 1710, 1615, 1580, 1410, 1375, 1350, 1285, 1230, 1210, 1170, 1115, 1065, 1005, 990, 965 | 3450, 2970, 2930, 1710, 1615, 1580, 1410, 1380, 1350, 1285, 1230, 1210, 1115, 1085, 1065, 1030, 990 |
| MW (FAB-MS) m/z | 730 (MH$^+$) | 672 (MH$^+$) |
| Molecular formula | $C_{37}H_{47}NO_{14}$ | $C_{34}H_{41}NO_{13}$ |

TABLE 5

1H-NMR and 13C-NMR chemical shifts of Compound A
Chemical Shifts are expressed as δ values (ppm)
with respect to tetramethylsilane (TMS)

| 1H-NMR data at 600 MHz, in dmso-d6 (ca. 4 mg/ml), at 28° C., Varian Unity-600 Spectrometer | | 13C-NMR data at 150 MHz, in dmso-d6 (ca. 4 mg/ml), at 28° C., Varian Unity-600 Spectrometer | |
|---|---|---|---|
| δ (ppm) | multiplicity, J (in Hz), n. of H, assignment | δ (ppm) | assignment |
| 1.01 | d, J=6.4, 3H, CH3–6' " | 16.5 | C-6' " |
| 1.12 | d, J=6.2, 3H, CH3–4" | 16.8 | C-6' |
| 1.18 | d, J=6.5, 3H, CH3–6' | 23.9 | C-4" |
| 1.57 | m, 2H, CH2–2' | 24.1 | C-14 |
| 1.58 | ddd, J=13.9, J=8.4, J=5.3, 1H, Hb-2" | 30.6 | C-5' " |
| 1.76 | ddd, J=13.9, J=5.3, J=4.9, 1H, Ha-2" | 31.6 | C-10 |
| 2.08 | dd, J=14.3, J=5.5, 1H, Heq-8 | 34.4 | C-2' |
| 2.10 | s, 3H, CH3–5' " | 35.9 | C-8 |

TABLE 5-continued

1H-NMR and 13C-NMR chemical shifts of Compound A
Chemical Shifts are expressed as δ values (ppm)
with respect to tetramethylsilane (TMS)

| 1H-NMR data at 600 MHz, in dmso-d6 (ca. 4 mg/ml), at 28° C., Varian Unity-600 Spectrometer | | 13C-NMR data at 150 MHz, in dmso-d6 (ca. 4 mg/ml), at 28° C., Varian Unity-600 Spectrometer | |
|---|---|---|---|
| δ (ppm) | multiplicity, J (in Hz), n. of H, assignment | δ (ppm) | assignment |
| 2.15 | dd, J=14.3, J=3.3, 1H, Hax-8 | 45.2 | C-3' |
| 2.27 | s, 3H, CH3–14 | 45.5 | C-3' " |
| 2.40 | dd, J=15.2, J=3.0, 1H, Hb-3' " | 46.1 | C-2" |
| 2.47 | dd, J=15.2, J=9.0, 1H, Ha-3' " | 56.5 | C-15 |
| 2.91 | m, 1H, CH-3' | 62.3 | C-3" |
| 2.92 | bs, 2H, CH2–10 | 66.8 | C-5' |
| 3.52 | bs, 2H, CH-4' | 69.5 | C-2' " |
| 3.79 | m, 1H, CH-3" | 69.7 | C-7 |
| 3.81 | dq, J=6.4, J=3.0, 1H, CH-1' " | 75.1 | C-4' |
| 3.91 | dt, J=9.0, J=3.0, 1H, CH-2' " | 79.1 | C-1' " |
| 3.98 | s, 3H, CH3–15 | 100.1 | C-1' |
| 4.18 | q, J=6.5, 1H, CH-5' | 102.9 | C-1" |
| 4.37–4.40 | two broad signals, 2H, OH-3" and OH-2' " | 110.6 | C-5 or C-11a |
| 4.68 | t, J-5.3, 1H, CH-1" | 110.7 | C-5 or C-11a |
| 4.92 | dd, J=5.5, J=3.3, 1H, CH-7 | 118.9 | C-1 |
| 5.21 | t, J=2.0, 1H, CH-1' | 119.6 | C-3 |
| 5.43 | bs, 1H, OH-9 | 120.0 | C-4a |
| 7.64 | dd, J=6.0, J=3.5, 1H, CH-3 | 134.4 | C-6a or C-10a or C-12a |
| 7.90 | m, 2H, CH-1 and CH-2 | 134.7 | C-6a or C-10a or C-12a |
| 13.2 | bs, 1H, OH-11 | 135.5 | C-6a or C-10a or C-12a |
| 13.9 | bs, 1H, OH-6 | 136.1 | C-2 |
| | | 154.4 | C-11 |
| | | 160.0 | C-6 |
| | | 160.7 | C-4 |
| | | 186.3 | C5 and C-12 |
| | | 211.6 | C-13 |

TABLE 6

1H-NMR and 13C-NMR chemical shifts of Compound B
Chemical Shifts are expressed as δ values (ppm)
with respect to tetramethylsilane (TMS)

| 1H-NMR data at 600 MHz, in dmso-d6 (ca. 2 mg/ml), at 28° C., Varian Unity-600 Spectrometer | | 13C-NMR data at 150 MHz, in dmso-d6 (ca. 2 mg/ml), at 28° C., Varian Unity-600 Spectrometer | |
|---|---|---|---|
| δ (ppm) | multiplicity, J (in Hz), n. of H, assignment | δ (ppm) | assignment |
| 1.14 | d, J=6.3, 3H, CH3–6" | 17.2 | C-6' and C-6" |
| 1.17 | d, J=6.5, 3H, CH3–2' " | 22.2 | C-2' " |
| 1.18 | d, J=6.8, 3H, CH3–6' | 23.7 | C-14 |
| 1.47 | dd, J=12.6, J=3.9, 1H, Heq-2' | 31.5 | C-10 |
| 1.57 | dt, J=12.6, J=3.9, 1H, Hax-2' | 34.2 | C-2' |
| 1.90 | dt, J=6.8, J=2.7, 1H, CH-3" | 36.0 | C-8 |
| 2.11 | dt, J=14.3, J=5.6, 1H, Hb-8 | 45.6 | C-3' |
| 2.15 | dd, J=14.3, J=4.6, 1H, Ha-8 | 56.4 | C-15 |

TABLE 6-continued

1H-NMR and 13C-NMR chemical shifts of Compound B
Chemical Shifts are expressed as δ values (ppm)
with respect to tetramethylsilane (TMS)

| 1H-NMR data at 600 MHz, in dmso-d6 (ca. 2 mg/ml), at 28° C., Varian Unity-600 Spectrometer | | 13C-NMR data at 150 MHz, in dmso-d6 (ca. 2 mg/ml), at 28° C., Varian Unity-600 Spectrometer | |
|---|---|---|---|
| δ (ppm) | multiplicity, J (in Hz), n. of H, assignment | δ (ppm) | assignment |
| 2.25 | s, 3H, CH3–14 | 61.3 | C-3" |
| 2.88 | dq, J=12.6, J=3.9, 1H, CH-3' | 65.4 | C-1'" |
| 2.90 | d, J=17.0, 1H, Hb-10 | 67.0 | C-5' |
| 2.99 | d, J=17.0, 1H, Ha-10 | 69.5 | C-7 |
| 3.26 | t, J=8.0, 1H, CH-4" | 77.0 | C-5" |
| 3.42 | d, J=3.9, 1H, CH-4' | 77.9 | C-4" |
| 3.62 | quintuplet, J=6.5, 1H, CH-1'" | 79.4 | C-4' |
| 3.81 | dq, J=8.0, J=6.3, 1H, CH-5" | 100.3 | C-1' |
| 4.00 | s, 3H, CH3–15 | 105.4 | C-2" |
| 4.10 | q, J=6.8, 1H, CH-5' | 118.9 | C-1 |
| 4.67 | broad signal, 2H, OH-4" and OH-1'" | 119.6 | C-3 |
| 4.93 | d, J=2.7, 1H, CH-2" | 136.0 | C-2 |
| 4.95 | t, J=4.6, 1H, CH-7 | | |
| 5.21 | d, J=3.4, 1H, CH-1' | | |
| 5.45 | bs, 1H, OH-9 | | |
| 7.65 | dd, J=7.0, J=2.4, 1H, CH-3 | | |
| 7.92 | m, 2H, CH-1 and CH-2 | | |
| 13.25 | bs, 1H, OH-11 | | |
| 13.85 | bs, 1H, OH-6 | | |

N.B.: no direct 13C-NMR data, only indirectly detected CHn from HMQC experiment

What is claimed is:

1. An anthracycline glycoside of formula I

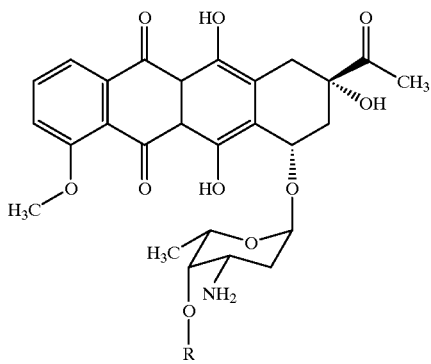

wherein R represents one of the two following residues:

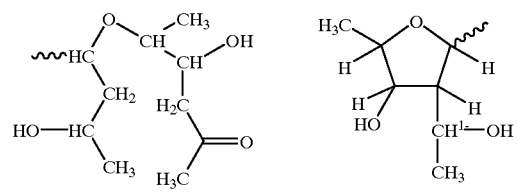

or a pharmaceutically acceptable salt thereof.

2. A salt according to claim 1 which is the hydrochloride salt.

3. A compound according to claim 1 which is 4'-O-[3"-hydroxy-1"-(2'"-hydroxy-1'"-methyl-4'"-oxo-pentyloxy)-butyl]-daunorubicin or 4'-O-[4"-hydroxy-3"-(1'"-hydroxy-ethyl)-5"-methyl-tetrahydro-furan-2-yl]-daunorubicin.

4. A process for the preparation of an anthracycline glycoside of formula I as defined in claim 1 or a pharmaceutically acceptable salt thereof, which process comprises culturing *Streptomyces peucetius* ATCC 27952 and isolating a resultant anthracycline glycoside of formula I as such or in the form of a pharmaceutically acceptable salt thereof.

5. A pharmaceutical composition comprising a pharmaceutically effective amount of an anthracycline glycoside of formula I as defined in claim 1, or a pharmaceutically acceptable salt thereof; and a pharmaceutically acceptable carrier or diluent.

6. A method of treating tumors, comprising administering an effective amount of the anthracycline glycoside of claim 1, or a pharmaceutically acceptable salt thereof, to a human or an animal in need thereof.

7. A method of therapeutically treating a human being or an animal, comprising:
   administering a therapeutically effective amount of the anthracycline glycoside compound of formula 1 of claim 1 or a pharmaceutically acceptable salt thereof in a pharmaceutically acceptable carrier or diluent to said human being or animal, thereby treating gram positive or gram negative bacterial infections or inhibiting growth of tumor cells.

8. The method of claim 7, wherein the pharmaceutically acceptable salt is the hydrochloride salt of said anthracycline glycoside compound.

9. The method of claim 7, wherein said compound is 4'-O-[3"-hydroxy-1"-(2'"-hydroxy-1'"-methyl-4'"-oxo-pentyloxy)-butyl]-daunorubicin or 4'-O-[4"-hydroxy-3"-(1'-hydroxyethyl)-5"-methyl-tetrahydrofuran-2-yl}-daunorubicin.

10. The method of claim 7, wherein the therapeutic utility of the anthracycline glycoside compound is as an anti-tumor agent.

* * * * *